United States Patent [19]

Terry

[11] Patent Number: 4,861,156
[45] Date of Patent: Aug. 29, 1989

[54] VISUAL ACUITY TESTING SYSTEM

[76] Inventor: Clifford M. Terry, 1733 Rocky Rd., Fullerton, Calif. 92635

[21] Appl. No.: 93,603

[22] Filed: Sep. 8, 1987

Related U.S. Application Data

[63] Continuation of Ser. No. 666,996, Oct. 31, 1984, abandoned.

[51] Int. Cl.$^4$ ............................................. A61B 3/02
[52] U.S. Cl. ..................................... 351/243; 351/246
[58] Field of Search ............... 351/237, 243, 244, 221, 351/246

[56] References Cited

U.S. PATENT DOCUMENTS

| | | | |
|---|---|---|---|
| 1,698,013 | 1/1929 | De Zeng | 351/242 |
| 2,190,008 | 2/1940 | Beitel | 351/242 |
| 2,937,567 | 5/1960 | Hardy et al. | 351/242 |
| 4,239,351 | 12/1980 | Williams et al. | |
| 4,293,200 | 10/1981 | Dobson et al. | 351/243 |
| 4,526,452 | 7/1985 | Hirsch | 351/243 |

FOREIGN PATENT DOCUMENTS 113918 9/1980 Japan .................................. 351/242

OTHER PUBLICATIONS

"B-VAT Video Acuity Tester", advertisement.
"Hoya Vision Chart"-advertisement, Jan. 1982.
"A Computer-Based Automatic Method for Determining Visual Acuity", Edward R. F. W. Crossman et al, pp. 344-355, Dec. 1969.

Primary Examiner—Rodney B. Bovernick
Attorney, Agent, or Firm—Laff, Whitesel, Conte & Saret

[57] ABSTRACT

A visual acuity testing system includes a patient video display operated under control of a compact control unit which is located adjacent the phoropter used in acuity testing. The control unit and phoropter are located in a common operating area, thus eliminating the need to shift from one position to another to operate different devices during visual acuity testing. The control unit operates in conjunction with a graphics interface processor to provide random character generation, variable character contrast, duochrome testing, automatic timing of character display, audio prompting and generation of complex test patterns such as an astigmatic clock pattern. The use of high resolution bit-mapped and vector graphics generation techniques maximizes the quality of character displayed on the patient display unit.

14 Claims, 5 Drawing Sheets

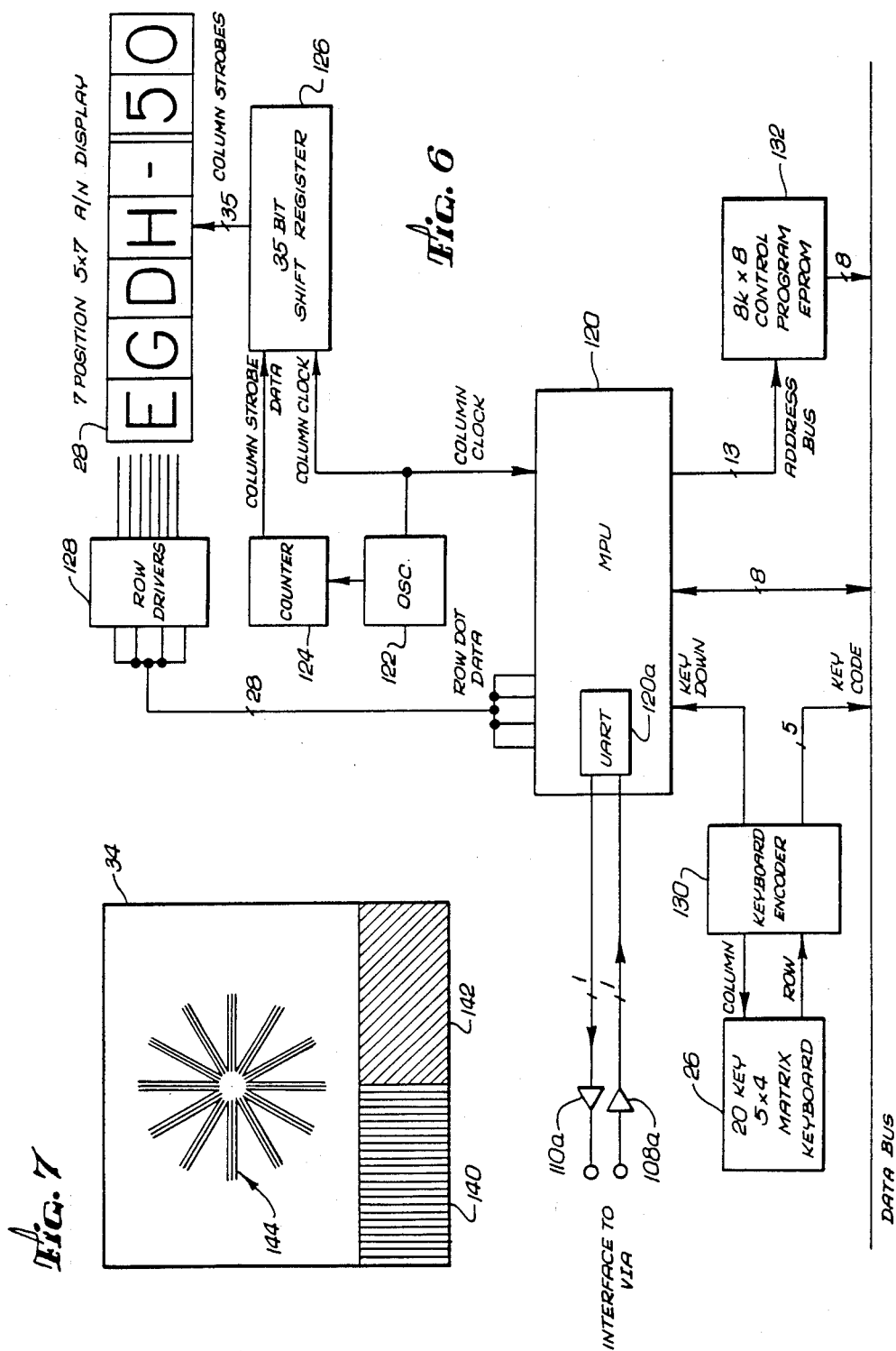

VISUAL ACUITY TESTING SYSTEM

This application is a continuation of prior application Ser. No. 6/666,996, filed Oct. 31, 1984, now abandoned.

BACKGROUND OF THE INVENTION

1. Field of the Invention

The present invention relates to a device for use in testing visual acuity contrast testing, glare testing, duochrome testing, and amblyopia testing.

2. Description of the Prior Art

The Snellen chart is the most widely used method for testing of visual acuity. Originally, a wall chart having a number of rows of characters of different sizes was employed. Subsequently, the projector chart was introduced, in which a single line of characters of a predetermined size is projected onto a screen. Testing is typically accomplished by having the patient view the chart through a phoropter, i.e., an optical device containing numerous lenses which may be selectively introduced into the line of vision of the patient. While the patient is viewing the projected eye chart, the phoropter controls are manipulated until a lens combination which achieves optimum vision is obtained. Whenever it is desired to change the size of the projected characters, the examiner must move away from the phoropter to operate the projector.

A major drawback of projector testing stems from the fact that the characters which are projected are fixed. The lenses of the phoropter are typically altered while having the patient view the minimum visible line in order to achieve refraction, i.e., selection of the proper lens combination for the patient. The repeated viewing of the same line leads to problems of memorization of the characters. The patient cannot subjectively distinguish between better vision resulting from a new lens combination and knowledge of the letters.

Acuity testing is typically accomplished in a small room, with the projector positioned next to the examiner and multiple mirrored paths of light being employed to achieve the necessary projection distance (approximately twenty feet) so that the light rays reaching the patient may be considered parallel. Because of the multiple mirrored paths of light, the examiner or other personnel in the room may get in the projection path. This is especially so in the case of the examiner, since the examiner must turn to the projector every time letter size is to be changed and then return to manipulate the phoropter dials.

In an attempt to overcome some of the disadvantages of the use of a projection chart for refraction, the system disclosed in U.S. Pat. No. 4,239,351 to Williams et al employs a video display for the purpose of displaying visual acuity targets to be viewed by the patient. An operator's control console contains control buttons for selecting the size of the targets to be displayed. The control console operates to generate letters in a random fashion, thus avoiding the problem of patient memorization of test letters. The control console includes its own video display, thus enabling the examiner to face in the general direction of the patient while selecting the targets to be generated and avoiding the need for the examiner to turn to see the targets displayed on the patient display unit. The video display unit of the control console is substantially the same size as that of the patient display unit and is in fact bulkier than the typical prior art projector unit. Although multiple mirrored projection paths are eliminated, the testing procedure is still awkward and inefficient, since the examiner must move away from the phoropter dials to the control console to select a new display.

Several features not possible with a standard projector are disclosed in the above-mentioned U.S. Pat. No. 4,239,351. These include the ability to project white targets on a black background, a zoom capability for continuously altering the size of the displayed targets, and means for controlling ambient light with respect to the patient display to enable acuity to be tested at more norma-1 levels of ambient illumination. However, the basic testing procedure is essentially identical to that employed with a standard projection system. Furthermore, target generation on the video display is accomplished by means of block graphics, in which each target is described by a 5×5 matrix of light and dark areas. The matrix is stored in memory and acted upon by an appropriate scale factor to achieve the desired target size. The use of block graphics limits the resolution of the system. In addition, it limits the types to targets which can be generated to those which may be defined in terms of blocks in the matrix.

SUMMARY OF THE INVENTION

The present invention incorporates numerous features which greatly increase the efficiency of and accuracy of the visual acuity testing procedure. The system includes a patient visual display and graphics display circuitry for generating acuity test character and other targets on the patient's display. The graphics display circuitry employs bit-mapped and vector graphics techniques for character generation. That is, characters are defined on a pixel-by-pixel or vector basis rather than being defined in terms of blocks as in the prior art. This enables a high degree of resolution to be achieved, and facilitates the provision of complex but extremely useful characters, and other targets such as an astigmatic clock.

Control of target generation is accomplished by means of a compact control unit which is mounted adjacent to the phoropter. The control unit is about the size of a typical hand-held electronic calculator and includes a display indicating the characters and size of characters currently displayed on the patient video display unit. By providing a compact control unit and mounting it adjacent to the phoropter, the necessity for the examiner to be constantly moving, from the phoropter over to a projector is eliminated. All adjustments which must be made during the visual acuity testing procedure, namely, phoropter adjustment and visual display adjustments, can be made without requiring any substantial shift in the examiner's position. The phoropter and display control unit in effect become an integrated system, with all controls necessary for the testing procedure being located in substantially the same location. It has been found that the examination time required for each patient may be reduced by several minutes, resulting in a savings of examination time of up to an hour per day for a typical office.

In addition to the configuration of the system of the present invention which facilitates an increase in testing efficiency, the present invention incorporates numerous features which increase the accuracy of visual acuity testing. One such feature is the inclusion of the capability in the control unit to vary the contrast of the patient video display Prior testing systems, including both the projection chart and prior systems employing display monitors, test under a single condition of maximum possible contrast, i.e., the blackest possible letters on the whitest possible background (and in some cases, the inverse situation). This, however, does not correspond to contrast levels encountered in everyday situations. Therefore, the testing of acuity under such contrast conditions may not result in the most accurate determination of the patient's acuity in typical conditions and corrective lenses which are prescribed may not be optimum. By providing a variable contrast control, the contrast of the display may be varied to simulate various actual conditions, thus enabling a more precise determination of acuity to be made. Critical vision situations, such as the reading of highway signs at night, may be simulated and vision corrected so as to be optimized for such situations.

An additional feature of the present invention is the provision of timing control of the character display so that characters may be automatically changed to a new set of characters of the same size after a predetermined time period so as to control patient fixation and accommodation. This eliminates the necessity for the examiner to be constantly reaching to the control unit to generate a new line of characters. This feature thus improves both the testing efficiency and accuracy.

Yet another feature of the present invention is the provision of colored filters over a portion of the patient display screen for the purpose of duochrome testing. White characters on a black background are generated in the display area beneath the filter. The letters thus take on the color of the filters, so that the resultant display is comprised of colored letters on a black background. This is to be contrasted with prior art duochrome test devices which employ black letters on colored backgrounds. Since the patient actually focuses on the letters, the provision of colored letters on a black background improves the testing procedure.

Another feature of the present invention is the inclusion of a glare lamp adjacent the patient video display. Since the characters to be read by the patient are not projected, the provision of a glare lamp adjacent the display will not alter the display itself The effect of glare on the patient's acuity can thus be effectively determined.

The testing device may also include an audio system which provides an audible signal each time the display is changed. The signal acts as a prompt to the patient to read the new display, thus further improving the efficiency of the testing procedure.

In order to facilitate the testing of children, the system of the present invention may include program controlled animation to achieve fixation. The animated display may be coupled with audio so as to further attract the attention of a child being tested.

BRIEF DESCRIPTION OF THE DRAWINGS

The invention will be described with reference to the accompanying drawings, wherein:

FIG. 6 is a block diagram of the control unit of the present invention; and

FIG. 7 is a diagram of an astigmatic clock display generated by the present invention.

DESCRIPTION OF THE PREFERRED EMBODIMENT

The following description is of the best presently contemplated mode of carrying out the invention. This description is made for the purpose of illustrating the general principles of the invention and is not to be taken in a limiting sense. The scope of the invention is best determined with reference to the appended claims.

Figure 1:
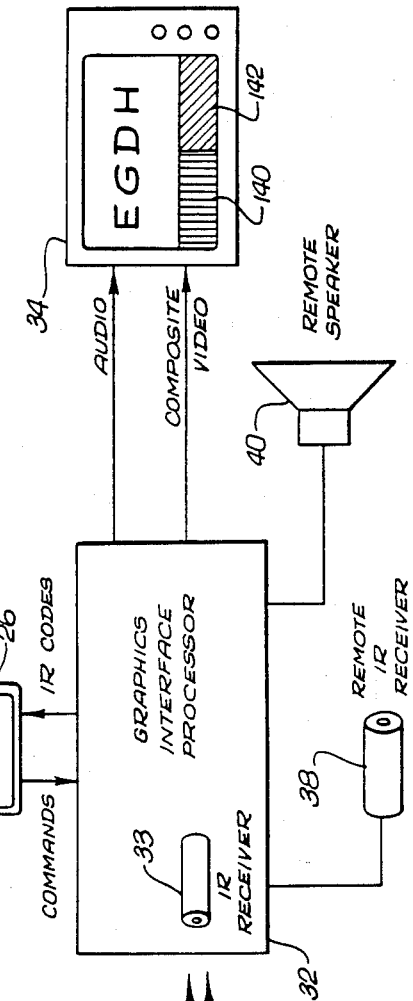
FIG. 1 is a top plan view of a typical examination room showing the present invention and its relation to the patient and phoropter.
Figure 1:
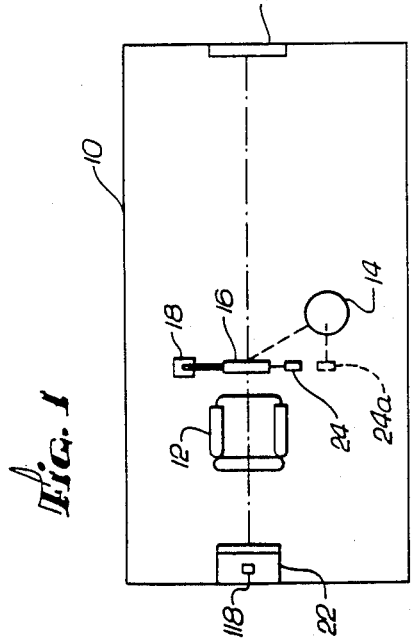

Referring to FIG. 1, a typical examination room 10 includes a patient chair 12 and an examiner's stool 14. A phoropter 16 mounted on a base 18 is positioned in front of the patient. The patient looks through the phoropter 16 toward a mirror 20 and views a reflected image from a patient video display 22. In order to properly test acuity, the patient should view parallel light rays, which implies that the video display which displays the visual acuity targets should be a minimum of about twenty feet from the patient. The use of mirrored lanes such as shown in FIG. 1 eliminates the necessity of having a long room to facilitate testing. When such a mirrored lane is employed, the characters are displayed in a reverse fashion, so that they will appear proper after reflection from the mirror 20. The display 22 is located above the patient and is positioned relative to the mirror 20 so that the patient can view the reflection of the display from the seat 12.

Figure 2:
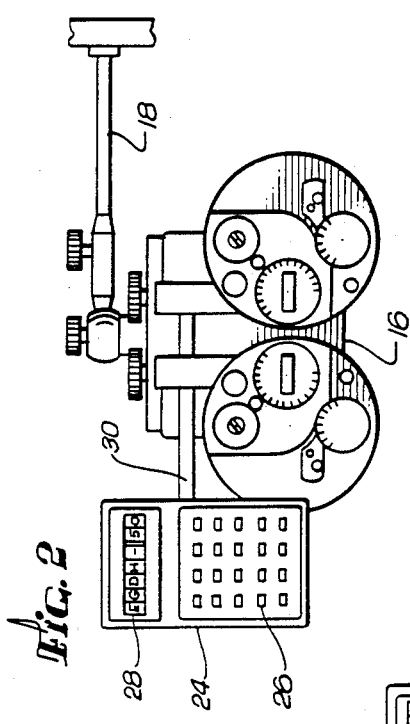
FIG. 2 is a front plan view of a phoropter and the control unit of the present invention mounted to the phoropter.

The generation of characters on the video display unit 22 is controlled by means of a compact control unit 24 which may be directly mounted to the phoropter 16 or may be mounted on a stand and positioned closely adjacent the phoropter 16 as indicated at 24a. As can be seen in FIG. 2, the control unit 24 includes a 4×5 matrix of control buttons 26 which are selectively activated to control the generation of characters on the patient's video display 22. In addition, the control unit includes a seven character LED display 28 which provides an indication corresponding to the characters presently displayed on the patient's video display. In the case of Snellen letters, the letters themselves will be displayed as well as a numerical indication indicating the size of the characters. For example, in FIG. 2, the letters E, G, D and H are displayed along with the numeral 50 to indicate that 20/50 size characters are being displayed. For patient displays not employing letters, the LED display 28 will provide information indicating the nature of the display.

The control unit 24 is shown in FIG. 2 attached directly to the phoropter 16 by means of a mounting bracket 30. During examination, the examiner must manipulate the phoropter 16 so as to vary the lens combination through which the patient views the display. The examiner must also manipulate the controls of the control unit 24 so as to alter the patient display. By providing a compact control unit and either attaching it directly to the phoropter or mounting it closely adjacent to the phoropter (as at 24a) the phoropter and control unit become essentially an integrated system. The examiner seated on the stool 14 can easily manipulate the controls of both the phoropter 16 and control unit 24 while remaining in the same position. The examiner simply moves his hand between the phoropter and control unit and need not turn away from the phoropter every time the patient display is altered. This is to be contrasted with a standard projector system in which the examiner must continuously turn away from the phoropter to change the characters being displayed. In the same fashion, the organization of the components of the present invention provides substantial efficiency improvements over prior systems employing a video display, since in such systems the control console includes a large video display monitor similar to the patient's video display and is a desktop or stand-alone system which cannot be conveniently positioned with respect to the phoropter. The provision of a compact control/display unit adjacent to the phoropter can result in a savings of several minutes in each examination, since the two functions which must be performed by the examiner, namely, phoropter manipulation and character display alteration, are for the first time both located within a single operating area.

Figure 3:
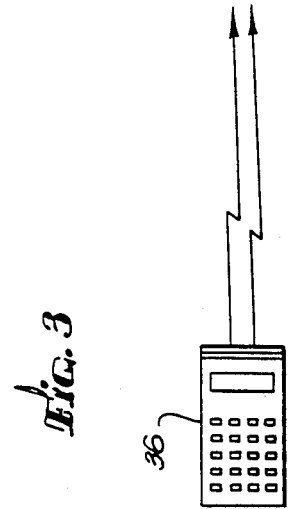
FIG. 3 is a block diagram of the system of the present invention.

FIG. 3 is a block diagram of the visual acuity testing system of the present invention. The control unit 24 is connected to a graphics interface processor 32 which, in combination with the control unit 24, controls the generation of characters to be displayed on a CRT monitor 34. The operating functions of the control unit 24 may be replicated on an infrared wireless transmitter 36 which enables the examiner to move around the examination room while still controlling the display. This may be convenient, for example, during an initial testing sequence when manipulation of the phoropter controls is not required. The graphics interface processor 32 includes an infrared receiver 33 to receive signals from the transmitter 36. In the event that an infrared wireless transmitter is employed and the graphics interface processor 32 is located in a concealed location, a remote infrared receiver 38 may be provided and located at a convenient position to receive signals from the transmitter.

In addition to a video display, the system of the present invention may incorporate an audio section to aid in the testing procedure. Audio signals are generated by the graphics interface processor and provided to an internal speaker of the CRT monitor 34 and alternatively may be provided to a remote speaker 40.

Both the control unit 24 and graphics interface processor 32 include microprocessors which interact to control the generation of characters on the patient display, as well as other functions of the system. The graphics interface processor 32 contains the majority of electronics employed to control character generation. Since it is remote from the control unit, its size is not critical.

The present invention employs bit-mapped and/or vector graphics for target or character generation. (The term "target character" as used herein means any visual acuity target to be displayed, including letters, numbers and additional patterns.) That is, each pixel of the CRT monitor is defined as white or black under program control to achieve the required character generation. Actual character selection is controlled by a microprocessor located in the control unit 24, whereas character generation is controlled by a microprocessor located in the graphics interface processor 32.

Figure 4B:
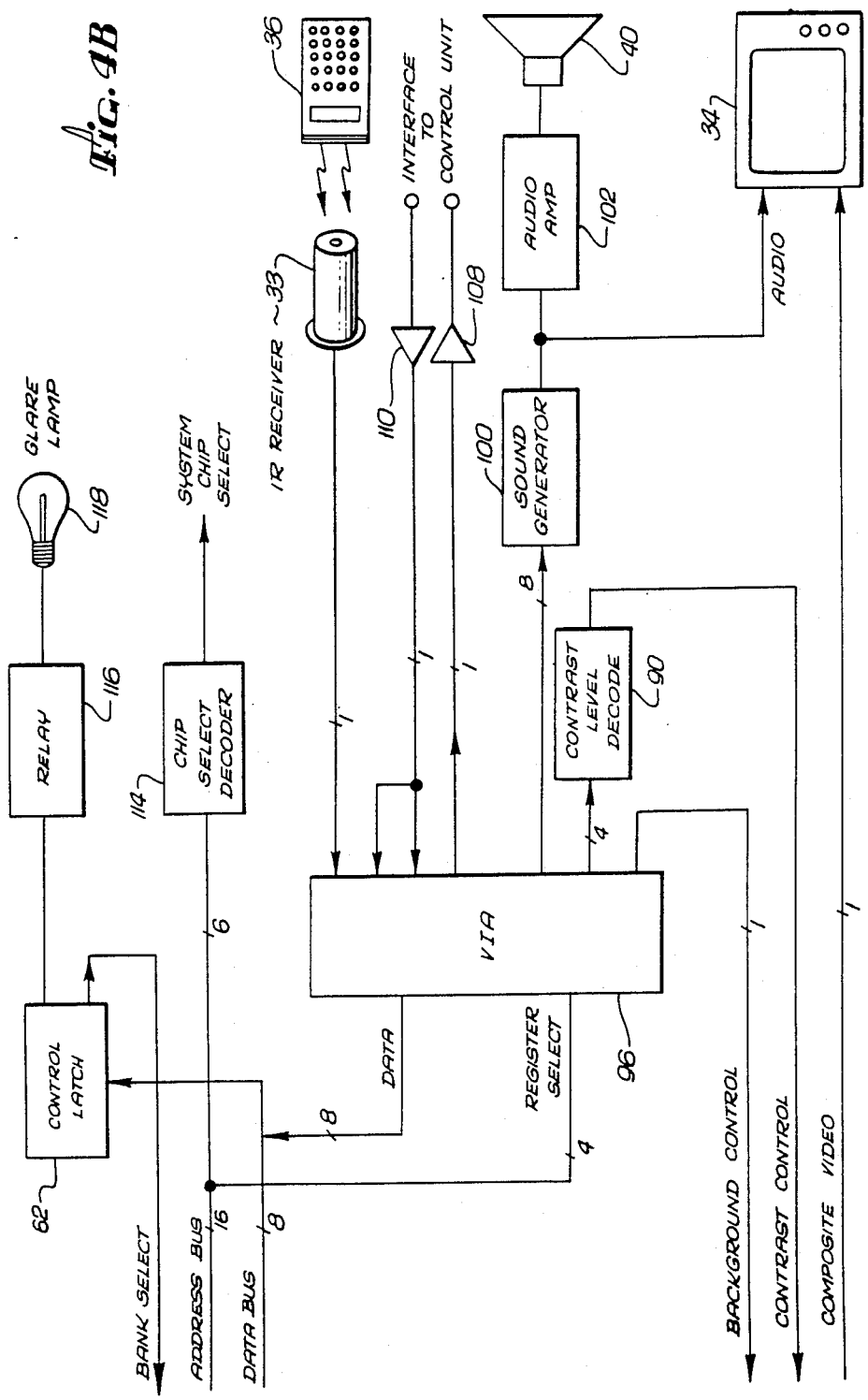
FIGS. 4A and 4B are block diagrams of the graphics interface processor of the present invention.
Figure 4A:
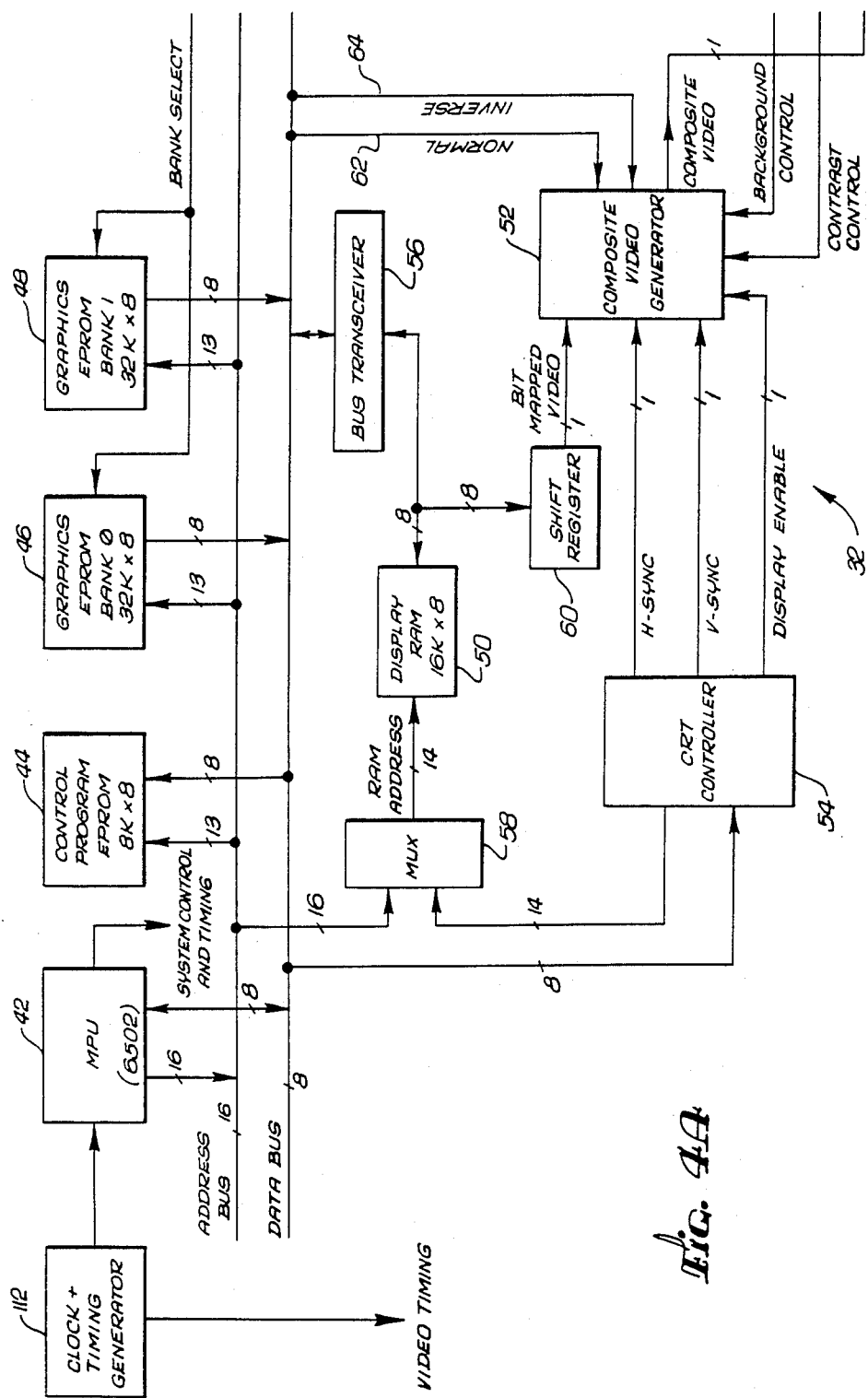

Referring to FIGS. 4A and 4B, the graphics interface processor 32 includes a microprocessor (MPU) 42 which controls character generation. An 8k×8 EPROM 44 contains the control program for the MPU 42. 32k×8 EPROMS 46 and 48 contain data representing the characters to be displayed. This data is transferred via the MPU 42 under program control to a 16k×8 display RAM 50. Information in the RAM 50 is provided to a composite video generator 52 which provides a composite video signal to the monitor 34 under control of a CRT controller 54.

The display RAM 50 contains data corresponding to the graphics pixels that form the various characters and patterns displayed on the CRT monitor 34 during visual acuity testing. That is, every pixel of the monitor 34 is defined as being either illuminated (a "1" bit) or not illuminated (a "0" bit) in a predetermined memory location in the RAM 50. The value of each pixel for a particular character is either stored in ROM (for bit-mapped) or determined under program control for vector graphics). In either case the display RAM 50 receives data regarding each pixel of the picture to be displayed. In the case of bit-mapped graphics, characters of the selected size are transferred from the permanent graphics memory ROM's 46 and 48 through bus transceiver 56 to the display RAM 50 under control of the MPU 42.

The RAM may be addressed via a multiplexer 58 by either the MPU 42 along an address bus or by the CRT controller 54. In operation, during a first portion of a program cycle of the MPU 42, the controller 54 addresses the display RAM 50 and display information is read from the RAM and loaded into a shift register 60 to serialize the video pixel information which is to be sent to the CRT monitor. The serialized bit-mapped video signal is supplied to the composite video generator 52 and a composite video signal is generated under control of the CRT controller 54. During a second portion of the program cycle of the MPU 42, the MPU 42 addresses the display RAM 50 for purposes of erasures, graphics transfers or pattern generation For example, data representing a new character may be transferred from one of the ROMs 46 and 48 into the display RAM 50 during this portion of the program cycle.

The CRT controller 54 is a conventional CRT video controller and provides all timing and control to refresh the CRT monitor 34. It provides the necessary sequential addressing for the display RAM 50, timing signals for the monitor 34 (including horizontal sync, vertical sync and display enable) and communication with the MPU 42. This communication merely allows the MPU 42 to configure the CRT controller 54 by loading operating parameters into its control registers. Changes to the display RAM 50 contents are accomplished by direct transfer from the processor to the RAM without any intervention by the CRT controller.

The MPU 42 addresses a memory space of 64k bytes. The total graphics memory also 64k bytes. In order to leave room for the control program, display RAM and memory-mapped input/output, graphics memory is selected one bank at a time, with each bank containing 32k bytes. Thus, whichever bank of the two banks 46 and 48 is needed for the current character size is selected under program control. This is accomplished by means of a control latch 62 which selects the necessary memory 46 or 48 in response to a control signal from the MPU 42. The control program EPROM 44 contains the control program software and is always enabled.

The total contents of the memories 46 and 48 contain the bit-mapped graphics representation of characters for the various sizes. Once the system has determined which randomly generated characters of which size it wishes to display, a verbatim block transfer is performed by the MPU 42, under program control, to move the EPROM-held graphics pixel data to the CRT display RAM 50. Vector graphics are employed for some of the larger characters and test patterns, such as the astigmatic clock pattern discussed below. Such characters are drawn, pixel by pixel, by special software routines each time they are to be displayed. They are not held in EPROM, as they would take up an excessive amount of space.

The ultimate composite video signal sent to the monitor 34 is a result of signals generated and modified by several circuits within the graphics interface processor. The video pixel information is transferred from the RAM 50 and converted into a serial pixel screen by the shift register 60. Normal and inverse control signals at 62 and 64 determine whether a normal video signal comprised of black letters on a white background or inverse video signal comprised of white letters on a black background are to be sent to the monitor. In addition, control signals including horizontal sync, vertical sync and display enable (blanking) are received from the CRT controller 54. Finally, control signals to set the contrast and background level of the composite video picture are also received by the video generator 52.

Figure 5:
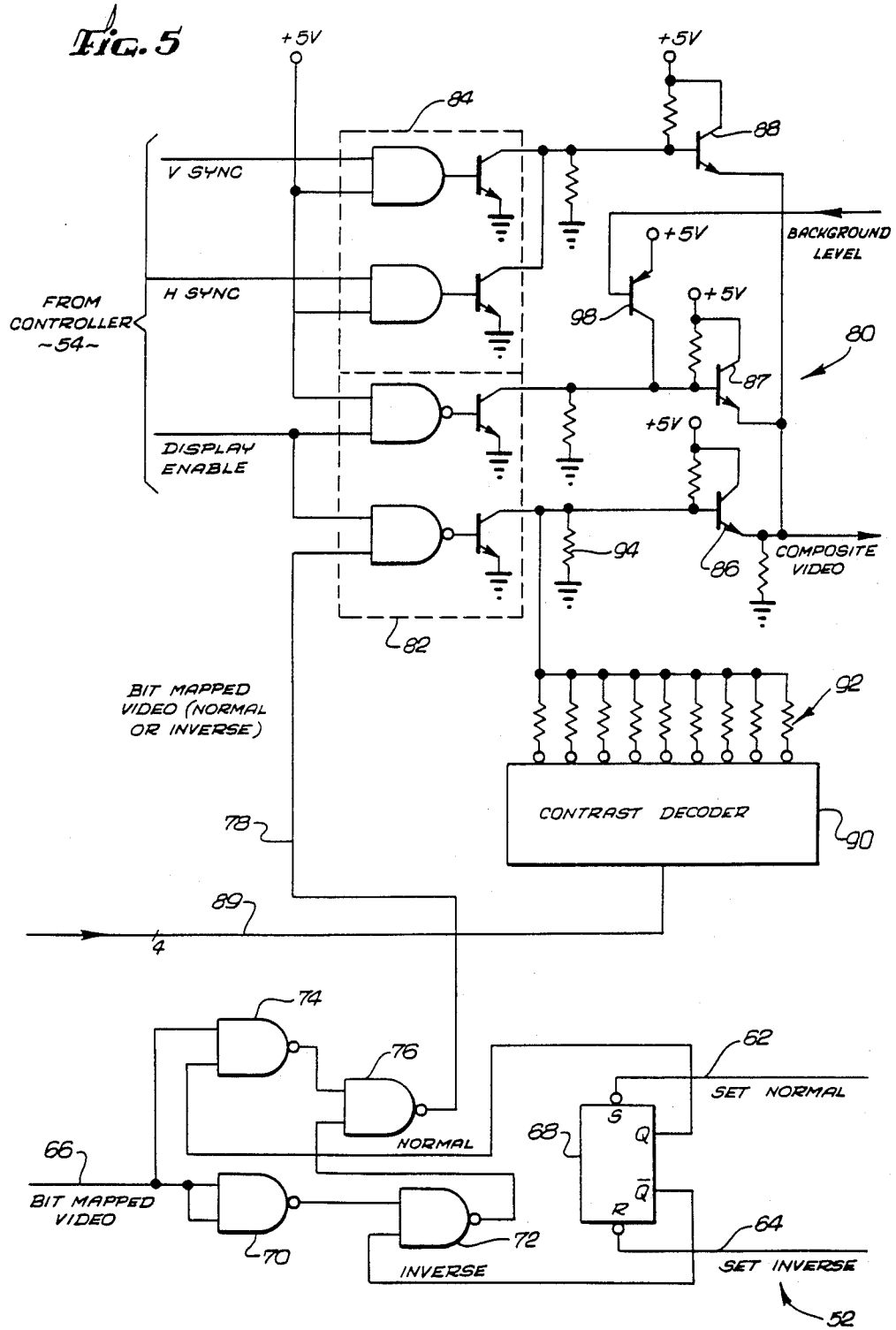
FIG. 5 is a schematic diagram of the composite video generator of the present invention.

The composite video generator 52 is shown in greater detail in FIG. 5. The pixel-by-pixel video signal from the shift register 60 is received along line 66. A flip-flop 68 and group of NAND gates 70–76 are employed to transfer the video signal in either a normal or inverted fashion along the line 78 to a video combining section 80. Integrated circuits 82 and 84 receive the video control signals from the controller 54 as well as the normal or inverted bit-mapped video signals. A composite video output is provided at the emitter of output transistors 86, 87 and 88.

An important feature of the present invention is the ability to selectively control the contrast and luminosity of the patient's video display. By incorporating this feature, the present invention enables testing which simulates critical visual situations. Contrast testing is important in early diagnosis of diseases of the eye. In addition, the ability to read highway signs at night is critical, and the present invention enables the lighting and contrast situation of such conditions to be simulated (i.e., both the background and foreground have the same luminosity as typical highway signs at night). A four-bit control signal representing the desired contrast level is delivered along a line 89 to a contrast decoder 90. The decoder selects one of a plurality of resistors 92 to connect in parallel with a resistor 94 so as to control the drive level to the base of the transistor 86, thus controlling the intensity of a "white" output Normally, the circuit 80 generates a "whitest" level video signal to correspond to a lighted pixel and a "blackest" level video signal for an unlighted pixel. The contrast decoder 90 and resistors 92 function to reduce the "white" level voltage by amounts corresponding to the selected contrast level. The four-bit contrast level on line 89 is provided by the MPU 42 through a Versatile Interface Adapter (VIA) 96 (FIG. 4B).

In addition to providing the control level signal, the VIA 96 provides a background level signal when operates to turn on a transistor 98 in the composite video generator 80 to change the background level from its "blackest" level to a fixed grey level. This is accomplished by providing increased drive to the transistor 87 by means of the transistor 98 so as to partially illuminate all pixels. Thus, whereas the contrast decoder 90 operates only on the white pixels, the background level control transistor 98 operates on the black pixels. In this fashion, both the contrast level and overall intensity of a simulated target (such as a highway sign) may be more closely approximated.

Referring back to FIG. 4, the VLA 96 is a parallel interface chip functioning as a general purpose input/output device and may be programmed by the MPU 42 to provide the desired interface functions. In addition to the contrast and background control for the composite video generator previously described, the VIA 96 provides signals to a sound generator 100 which generates audio tones to be provided to the internal speaker of the monitor 34 or to an audio amplifier 102 and external speaker 40. The sound generator can be used to provide a tone upon the changing of the video display. This functions as a prompting signal for the patient, thus avoiding the necessity of the examiner instructing the patient to read the new display. Furthermore, the sound generator is such that melodies and other complex sounds can be generated, which is useful, for example, when testing children in order to attract their attention. Operating parameters such as tone generator selection, frequency determination and volume settings are transferred in 8-bit parallel words from the MPU 42, under program control, via the data bus to the VIA 96, and from the VIA 96 to the sound generator 100.

The VIA 96 also operates as an interface for the infrared receiver 33 which receives signal from the wireless transmitter 36. In addition, the VIA 96 serves as an interface to the control unit 24. Bidirectional communications between the graphics interface processor and the control unit are accomplished over a full duplex serial interface conforming to the electrical specifications of EIA Standard RS422. The communications are asynchronous, bit serial, with a frame format of one start bit followed by eight data bits, followed by two stop bits at a BAUD rate of approximately 9,000 BAUD. IC's 108 and 110 comprise the RS422 transmitter and receiver, respectively. The data for transmission from the graphics interface processor to the control unit is generated and encoded entirely under software control. The receive data signal from the control unit to the graphics interface processor is fed into a control input in the VIA which generates an interrupt at the leading edge of the start bit to flag the start of an incoming message. The data signal is also input to a data input, where it is sampled, assembled and decoded entirely under software control.

Additional components in the graphics interface processor include a clock and timing generator 112 which generates a basic 10 MHz clock signal for video timing and also lower frequency clock signals used for the MPU 42. A chip select decoder 114 is controlled by the MPU to enable desired components in the system during various phases of operation.

One output of the control latch 62 is used as a bank select to select which memory 46 and 48 is to be coupled to the microprocessor 42. An additional output of the control latch 62 is coupled to a relay 116 which is energized to turn on a glare lamp 118. As shown in FIG. 1, the glare lamp 118 is positioned adjacent to monitor 22. Many patients have complaints of glare, with the primary difficulties being related to spot glare which originates in a single point. The glare lamp 118 provides spot glare to facilitate testing of the patient's sensitivity to glare. Preferably, the lamp is less than 10° away from the characters which the patient is viewing. Since the examiner is able to select different contrast ratios between the letters and the background and can select the size of the letters, the patient's acuity in a glare situation can be accurately determined. This glare test is very effective in determining patients with early cataracts and their eye diseases.

A block diagram for the control unit 24 is shown in FIG. 6. As previously mentioned, the control unit is located near the patient being examined and contains numerous control buttons to allow the examiner to select the various available displays and modes of operation. The control unit also contains the alphanumeric display 28 which indicates the characters, sizes and patterns that are currently being displayed. The control unit contains its own microprocessor 120 which, under program control, determines the random character pattern so that an unpredictable string of characters will appear each time a new line of characters is requested. The control program is stored in an 8k×8 EPROM 132. The control unit transmits the codes for the selected characters, character size information, and any mode commands to the graphics interface processor 32 in response to various key depressions. Even control messages from the wireless transmitter 36 are first sent to the control unit, which interprets them and then sends a message to the graphics interface processor directing its next action.

The control unit hardware accomplishes the functions of display generation, keyboard scanning and key code generation, and serial communication with the graphics interface processor. All other control unit functions are under the control of the resident MPU 120 and its control program.

An oscillator 122 generates a 2 millisecond clock which is used to time the essentially 7 row by 35 column display 28 in a multiplexed drive configuration. The oscillator 122 increments a decade counter 124, which issues a column strobe signal every ten clock pulses. The column strobe signal is applied as a data input to a 35 bit shift register 126 which is clocked by the column clock signal from the oscillator 122. Thus, at any point in time, a "1" will be contained in three locations in the shift register 126. As the column strobe signal is shifted through the shift register, the columns of the alphanumeric display 28 will be sequentially enabled. The column clock signal from the oscillator 122 is also applied to the MPU 120, which provides row information to row drivers 128 corresponding to the enabled columns. That is, when it is determined from the column clock signal that it is time for the next column's dot pattern to be presented, the MPU performs a character code to dot pattern conversion and presents the row dots for the currently strobed column to the display 28 via the row drivers 128. Thus, the MPU 120 is in active and constant involvement with the generation of the character display on the control unit.

The keyboard 26 is a twenty key 5×4 matrix keyboard which is constantly scanned by a keyboard encoder 130. The encoder detects when any key is depressed and generates a "key down" signal to the MPU 120. A key code corresponding to the depressed key is generated and provided to the MPU. After the MPU is informed that a new key has been depressed by means of the key down signal, the MPU then inputs the key code and takes whatever action is indicated by the specific key, including changing the display 28 and transmitting information to the graphics interface processor for character generation on the patient display. This information is sent via a UART 120a that is internal to the microprocessor 120.

The program control of character generation can include a keyboard-activated timed line feature, in which a line of characters of a particular size is automatically replaced by a new line of characters of the same size after a predetermined interval of time. This feature provides the dual advantages of maximizing patient fixation and accommodation to increase the accuracy of the testing procedure, and eliminating patient memorization when the patient is required to read the characters of a particular size a number of times. The provision of this feature thus can result in substantial improvements in testing accuracy. It is particularly useful in the presentation of tumbling E's, i.e. the display of an "E" in various orientations. This character is used in testing for amblyopia.

As shown in FIG. 3, the CRT monitor 34 includes red and green filters 140 and 142 along the bottom of the display. Under program control (and initiated by the control unit 24), white letters on a black background can be generated at a location under the filters to generate red and green letters on a black background for purposes of duochrome testing. Duochrome testing is known in the art and is based on the fact that the eye will focus on different colors at different focuses due to chromatic aberrations of the lens system. In prior art systems, black letters are generated on red and green background and the patient is asked to focus on the letters. Since the focus on the two colors is different, the edges of the letters will be blurred with one of the colors more than the other and the characters will look less black when the eye focus is not in the middle of the chromatic interval between red and green. In the present invention the patient actually focuses on the color of the letters rather than on black. As a result, edge blurring is much more apparent than with prior art systems. To the patient it appears that lines are radiating off of letters when they are out of focus. The lines disappear when equal focus is achieved Clinical investigation has indicated that the present duochrome test is more accurate than prior art tests. It should be noted that the duochrome test need not be a part of the overall testing system, but could be provided independently.

By employing high resolution bit-mapped and/or vector graphics, the present invention enables characters to be precisely generated and in addition enables complex characters such as an astigmatic clock test pattern as shown in FIG. 7, to be generated. The astigmatic clock consists of thirty-six substantially radial lines 144 extending from a central point and divided into groups of three, with the lines in each group being parallel to one another. Each group is spaced at 30° intervals. Because of the large number of pixels involved in the generation of an astigmatic clock display, the pixel-by-pixel information is not stored in memory. Rather, the pixel string locations for each radius are derived under program control by starting at an inner end point, provided from a table in memory, and then locating each successive pixel within the string a fixed $\Delta x$ and $\Delta y$ number of pixels from the preceding pixel. The outer end points are detected when the sum of the $\Delta x$ and $\Delta y$ increments equals the total $\Delta x$ and $\Delta y$ values for that string. The strings are drawn one string at a time, proceeding in a counterclockwise direction. An error minimizing routine makes minor adjustments to the "next pixel" position in order to have the pixel path oscillate about an ideal radius vector. Since deviation errors occur on both sides of the ideal vector, the average error is near zero.

The astigmatic clock generation is a prime example of the benefits to be derived by using high resolution graphics in the generation of characters as opposed to block graphics as employed in the prior art. By using high resolution graphics, numerous characters in addition to the basic Snellen characters may be generated. In a case of the astigmatic clock, the need for a separate test instrument for presenting such a display is eliminated. In addition, the microprocessor control combined with high resolution graphics enables animated scenes and the like to be presented on the display. The generation of animated scenes is very useful in the testing of small children who cannot read a Snellen chart. In such instances testing is accomplished by examining the child's eyes while the child is fixated on a distant object. The animated display generated with the present system is very effective in achieving fixation. This display may be coupled with music (also generated under program control) to further increase its effectiveness.

In summary, the present invention incorporates numerous features which facilitate both more efficient and more accurate testing of visual contrast testing, duochrome testing, and amblyopia testing acuity. This is accomplished by the provision of a compact control unit adjacent the phoropter and microprocessor control of the generation of high resolution graphics to take advantage of the ability of a video display to incorporate tests which were not previously available.

What is claimed is:

1. Vision testing apparatus comprising:
   a patient display;
   display circuitry for generating a plurality of alphanumeric character test targets on the patient display defined by first pixels illuminated to a first level of luminance, and second pixel illuminated to a second level of luminance;
   and means for varying the contrast of said target-defining pixels on the patient display including first controllable means for varying the luminosity of said first pixels, second controllable means for varying the luminosity of said second pixels, said first and second controllable means being operated independent of each other.

2. Apparatus as in claim 1 further comprising a control unit including means for manually controlling the operation of the display circuitry and the contrast of the patient display.

3. Apparatus as in claim 1 wherein the display circuitry includes means for varying the luminosity of the patient display.

4. Apparatus as in claim 1 wherein the contrast varying means generates a contrast control signal and the display circuitry includes microprocessor-controlled means for generating a pixel-by-pixel image signal and image generator means for receiving the image signal and the contrast control signal and providing a composite analog image signal of the desired contrast to the patient display.

5. Apparatus as in claim 1 wherein operation of said first and second controllable means varies the intensity of the test targets on said patient display independently of the intensity of the background of the test targets on the patient display.

6. Apparatus as in claim 1 wherein operation of said first and second controllable means varies the intensity of the background of the test targets on said patient display independently of the intensity of the test targets on the patient display.

7. The vision testing apparatus of claim 1 wherein:
   said first controllable means receives a first digital signal for selecting one of a plurality of predetermined luminosity levels for said first pixels; and
   said second controllable means receives a second digital signal for selecting one of a plurality of predetermined luminosity levels of said second pixels.

8. The vision testing apparatus of claim 7 wherein said first controllable means includes converter means to transform said first digital signal into an analog control voltage for controlling the luminosity of said first pixels.

9. The vision testing apparatus of claim 7 wherein said first controllable means further includes first output transistor means for providing an electrical signal indicative of the luminosity of said first pixels when each of said first pixels is to be displayed on said patient monitor.

10. The vision testing apparatus of claim 8 including:
    bias control means to establish a bias voltage applied to said first output transistor; and
    decoder means responsive to said first digital signal to select an individual one of a plurality of resistor means and to operatively connect said selected resistor means in parallel with said bias control means to alter said bias voltage as a function of said first digital signal.

11. The vision testing apparatus of claim 7 wherein said first digital signal is controlled by a microprocessor.

12. The vision testing apparatus of claim 7 wherein said second controllable means includes:
    second output transistor means for providing an electrical signal indicative of the luminosity of said second pixels when each of said second pixels is to be displayed on said patient monitor;
    bias control means to establish a bias voltage applied to said second output transistor; and
    control transistor means responsive to said second digital signal to alter said bias voltage as a function of said second digital signal.

13. The vision testing apparatus of claim 7 wherein said second digital signal is controlled by a microprocessor.

14. The vision testing apparatus of claim 1 wherein:
    said apparatus is used in an examiner-administered test;
    said patent display is adapted to be viewed by the patient over an optical path long enough to provide substantially parallel light rays;
    said first and second controllable means exclusively under the control of said examiner.

* * * * *